(12) United States Patent
Agut Sanchez et al.

(10) Patent No.: US 8,980,866 B2
(45) Date of Patent: Mar. 17, 2015

(54) COMPLEX OBTAINED FROM HYALURONIC ACID OR A SALT THEREOF AND CHONDROITIN SULPHATE MIXTURES

(71) Applicant: Quimera Ingenieria Biomedica, S.L., Barcelona (ES)

(72) Inventors: Julian Agut Sanchez, Sant Cugat del Valles (ES); Carlos Fernandez Navarro, Rubi (ES); Joan Cos Trullas, Igualada (ES); Laura Ocana Safont, Lleida (ES)

(73) Assignee: Opko Lab Europe, S.L., Barcelona (ES)

( * ) Notice: Subject to any disclaimer, the term of this patent is extended or adjusted under 35 U.S.C. 154(b) by 0 days.

(21) Appl. No.: 13/683,001

(22) Filed: Nov. 21, 2012

(65) Prior Publication Data

US 2013/0143838 A1 Jun. 6, 2013

(30) Foreign Application Priority Data

Nov. 24, 2011 (EP) ..................................... 11190532

(51) Int. Cl.
| | | |
|---|---|---|
| *C08B 37/00* | (2006.01) | |
| *C08B 37/08* | (2006.01) | |
| *A61K 9/00* | (2006.01) | |
| *A61K 47/00* | (2006.01) | |
| *A61K 9/14* | (2006.01) | |
| *A61K 31/728* | (2006.01) | |
| *A61K 31/737* | (2006.01) | |

(52) U.S. Cl.
CPC ......... *C08B 37/0063* (2013.01); *C08B 37/0072* (2013.01); *C08B 37/0069* (2013.01); *A61K 9/0019* (2013.01); *A61K 9/0024* (2013.01); *A61K 47/00* (2013.01); *A61K 9/14* (2013.01); *A61K 31/728* (2013.01); *A61K 31/737* (2013.01)
USPC .......................................................... 514/54

(58) Field of Classification Search
CPC ............ C08B 37/0063; C08B 37/0069; C08B 37/0072; A61K 31/715; A61K 31/726; A61K 31/728
See application file for complete search history.

(56) References Cited

U.S. PATENT DOCUMENTS

| | | | | |
|---|---|---|---|---|
| 6,051,560 | A | * | 4/2000 | Chang et al. ..................... 514/54 |
| 7,820,194 | B2 | * | 10/2010 | Jafari et al. .................... 424/427 |
| 7,956,180 | B2 | * | 6/2011 | Bach et al. .................... 536/55.1 |
| 2013/0165404 | A1 | † | 6/2013 | De Rosa | |

FOREIGN PATENT DOCUMENTS

| | | |
|---|---|---|
| EP | 0136782 A2 | 4/1985 |
| WO | 02/30463 A2 | 4/2002 |
| WO | WO 2012032151 A1 * 3/2012 | ............. C08B 37/08 |

OTHER PUBLICATIONS

Nishimura, M. et al., "Role of Chondroitin Sulfate-Hyaluronan Interactions in the Viscoelastic Properties of Extracellular Matrices and Fluids," Biochimica Et Biophysica Acta—General Subjects, Elsevier Science Publishers, NL, vol. 1380, No. 1, Mar. 12, 1998, pp. 1-9, XP027200057.

European Search Report, Application No. EP 11190532, Place of Search: Munich, Date of completion: Feb. 24, 2012, 1 page.

\* cited by examiner
† cited by third party

*Primary Examiner* — Shaojia Anna Jiang
*Assistant Examiner* — Dale R Miller
(74) *Attorney, Agent, or Firm* — Rothwell, Figg, Ernst & Manbeck P.C.

(57) ABSTRACT

The present invention relates to a novel complex, obtainable by mixing hyaluronic acid or a salt thereof and chondroitin sulphate or a salt thereof, and forming an aqueous solution of said mixture, which is further subjected to a drying process. The invention also relates to various compositions and formulations comprising the complex of the invention, process for obtaining said complex and uses thereof.

18 Claims, 4 Drawing Sheets

COMPLEX OBTAINED FROM HYALURONIC ACID OR A SALT THEREOF AND CHONDROITIN SULPHATE MIXTURES

CROSS-REFERENCE TO RELATED APPLICATION

The present application claims the benefit of priority to European Patent Application No. EP 11190532.9, filed 24 Nov. 2011, which is incorporated herein by reference in its entirety.

TECHNICAL FIELD OF THE INVENTION

The present invention relates to a complex obtainable by mixing hyaluronic acid or a salt thereof and chondroitin sulphate or a salt thereof, and forming an aqueous solution of said mixture, which is further subjected to a drying process. The invention also relates to various compositions and formulations comprising the complex of the invention, process for obtaining said complex and uses thereof.

BACKGROUND OF THE INVENTION

Hyaluronic acid and chondroitin sulphate play an important role in the biological organism, especially as a main component of the intercellular matrix and mechanical support for many kinds of cells, such as those of the skin, tendons, muscles and cartilage. Hyaluronic acid and chondroitin sulphate also play other important parts in biological processes, such as the moistening of tissues, lubrication and mechanical loading.

Water soluble gel forming materials comprising hyaluronic acid or salts thereof are well-known and widely used in the health care sector, for example in ophthalmology, in the treatment of osteoarthritis, as well as in the pharmaceutical and cosmetics industries.

A number of chondroitin sulphate/hyaluronate compositions are known as viscous or viscoelastic agents for ophthalmic surgical use. Due to their particular physical characteristics, certain viscoelastic agents will be better suited for particular aspects of the surgical procedure. For example, in cataract surgery, it is commonly used the combination of relatively low molecular weight sodium hyaluronate and chondroitin sulphate. However, high molecular weight agents tend to be highly cohesive and, in general, very viscous solutions containing relatively high molecular weight agents, including high molecular weight sodium hyaluronate, are more effective in maintaining the intraocular space than less viscous solutions containing relatively lower molecular weight agents.

Viscoat (Alcon Laboratories, Inc.) is a viscoelastic solution which contains about 3% sodium hyaluronate and 4% chondroitin sulphate in a physiological buffer with a viscosity of 40,000±20,000 cps (at shear rate of 2 see and 25° C.), wherein the sodium hyaluronate used has a molecular weigh of 500,000 Daltons.

US 2011/0015151 discloses aqueous viscoelastic compositions for use in ophthalmic surgical procedures, comprising a combination of hyaluronic acid and chondroitin sulphate, wherein the hyaluronic acid has a molecular weight of 1,500,000 to 1,900,000 Daltons and is present at a concentration of 1.7% w/v. The chondroitin sulphate or ophthalmically acceptable salt thereof used has a molecular weight of 20,000 to 100,000 Daltons and is present at a concentration of 4% w/v.

Viscoelastic compositions have been also used in other surgical procedures, U.S. Pat. No. 6,632,423 describes a viscoelastic agent characterized by a viscosity of at least 30 Pa·s, comprising sodium hyaluronate and chondroitin sulphate, which is used as a packing material in middle ear surgery. The sodium hyaluronate has an average molecular weight of about 2.2 million Daltons and is present at a concentration of about 1.6% by weight. The chondroitin sulphate used has an average molecular weight of about 50,000 Daltons and is present at a concentration of about 4% by weight.

Less viscous sodium chondroitin sulphate/hyaluronate mixtures are suitable for other uses, such as the treatment of osteoarthritis, wherein the molecular weight of sodium hyaluronate is usually less than 1,000,000 daltons. A conventional treatment of osteoarthritis involves the intra-articular application of hyaluronate or chondroitin sulphate/hyaluronate mixtures. However, the effect of this treatment with conventional hyaluronate is usually temporal because the hyaluronate remains within the articular chamber for short time before it is absorbed and/or metabolized.

WO 03/041724 reveals intra-articular application of a mixture of 30 mg/mL sodium hyaluronate and 40 mg/mL sodium chondroitin sulphate for the management of osteochondral lesions of the knee inductor of chondrogenesis, to regenerate the cartilage destroyed by osteoarthritis. The sodium hyaluronate has a molecular weight of 500,000 to 1,000,000 Daltons, and the composition disclosed therein has a viscosity of 20,000 to 60,000 m·Pas (cps).

WO 2009/138843 discloses a glycosaminoglycan oral composition comprising (a) from 80 mg to 200 mg of hyaluronic acid or a pharmaceutically acceptable salt thereof having an average molecular weight of not less than 10,000 Daltons; and (b) from 150 mg to 500 mg of chondroitin sulphate or a pharmaceutically acceptable salt thereof having an average molecular weight of from 5,000 to 50,000 Daltons; in a mixture with a pharmaceutical carrier.

Furthermore. EP0136782 discloses an aqueous composition containing chondroitin sulphate and sodium hyaluronate for use as an active therapeutic material. The chondroitin sulphate/sodium hyaluronate solution is prepared in a buffer containing 5.3 g of chondroitin sulphate and 4.2 g of sodium hyaluronate in 100 mL of water, which has a viscosity at 25° C. 71,500 mPa·s.

Interestingly, addition of chondroitin sulphate to sodium hyaluronate in aqueous solution dramatically increases the viscosity of mixture (Nishimura et al., *Biochimica et Biothphysica Acta* 1380, 1-9 (1998)). This increase in viscosity appears to be mainly due to the increase in molecular weight rather than solute concentration increase.

Chondroitin sulphate has interesting biological properties for the treatment of joints and bones. The administration of exogenous chondroitin sulphate can enhance the production of newly synthesized ECM components, endogenous hyaluronic acid and proteoglycans (J. Y. Reginster et al., *Drugs aging* 24(7), 573-580, (2007)). It may suppress the production and activity of proinflammatory mediators and proteases, and there is evidence showing that chondroitin sulphate prevents the degradation of cartilage and may promote its regeneration (J. Y. Reginster at al., *Mini Rev. Med.* 7(10), 1051-1061 (2007) and Wildi at al., *Ann. Rheum. Dis.* 70(6), 982-989 (2011)).

Synovial fluid is primarily composed of high molecular weight sodium hyaluronate, the concentration of sodium hyaluronate in the normal human synovial joint fluid is approximately 3 mg/mL. In osteoarthritis patients, the concentration and molecular weight of sodium hyaluronate in synovial fluid decrease, resulting in the diminished capacity of the fluids to protect the cartilage. Additionally, high molecular weight hyaluronic acid formulations stimulate the synthesis of hyaluronic acid more than lower molecular weight formulations (M M. Smith et al., *Rheumatol. Int.* 7(3), 113-22 (1987)), reduce the production and activity of proinflammatory mediators and matrix metalloproteinases and maintains joints in good condition (H. Matsuno, et al., *Inflamm. Res.* 48, 154-159 (1999), M. Goto et al., *Clin. Exp. Rheumatol* 19, 377-383 (2001) and L. Morelans et al., *Arthritis Res. Ther.* 5, 54-67 (2003)).

Therefore, more concentrated mixtures or formulations comprising high molecular weights sodium hyaluronates are expected to be more effective but also highly viscous and consequently unsuitable for some routes of administration or applications such as intra-articular injection. For example, current formulations for the treatment of osteoarthritis are generally administered at 2 to 6 doses over 1 to 3 months at 7-20 day intervals in order to reach an acceptable therapeutic effect. The main reported adverse event of this treatment is pain in the injection site, caused mainly by the high viscosity of the formulations injected. This problem inevitably limits the molecular weight of the hyaluronic acid used and/or the quantity of hyaluronic acid and chondroitin sulphate to be injected.

In view of the above, there is still a need to develop new pharmaceutical compositions comprising hyaluronic acid and chondroitin sulphate, exhibiting a lower viscosity while maintaining their known therapeutically effects, thus allowing an improvement in the treatment of patients.

EXPLANATION OF THE INVENTION

After thorough research, the inventors have surprisingly found that the aforementioned problems can be solved by using the complex according to the aspects and embodiments of the present invention and characterized herein below in the appended examples and claims.

The present invention relates to a complex obtainable by mixing hyaluronic acid or a salt thereof, and chondroitin sulphate or a salt thereof, this mixture is firstly dissolved in an aqueous solvent to form a solution, which is further subjected to atomization according to claim 1.

The claimed complex solves the aforementioned technical problem by providing new compositions containing high molecular weight hyaluronates or higher concentrations of chondroitin sulphate and sodium hyaluronate, which allow new effective applications and treatments with a lower incidence of adverse events.

Indeed, the complex of the present invention provides, on the one hand, more concentrated compositions containing sodium chondroitin sulphate and sodium hyaluronate with a limited increase in viscosity of the resulting concentrated composition, even with high molecular weight hyaluronates.

On the other hand, compositions comprising the complex of the present invention were formulated at typical concentrations of commercial products available in the market but having a considerable lower viscosity.

Without wishing to be bound by any theory the process described herein is believed to form a complex in which the hyaluronic acid, or a salt thereof, is bound to chondroitin sulphate or a salt thereof without significantly changing the chemical character of either the hyaluronic acid, or a salt thereof, or the chondroitin sulphate or a salt thereof. The atomization process in accordance with the present invention causes the mixture to associate and to form a complex with a significant conformation change.

Therefore, as used herein the complex of the present invention refers to the resulting dried product formed after atomizing an aqueous solution containing a mixture of hyaluronic acid or a salt thereof, and chondroitin sulphate or a salt thereof. Furthermore, the complex obtained by the process described herein is structurally different from a simple mixture of hyaluronic acid or a salt thereof, and chondroitin sulphate or a salt thereof and cannot therefore be considered as a simple mixture of both compounds. However, said process does not change the chemical character of either the sodium hyaluronate or the chondroitin sulphate, as high performance liquid chromatography (HPLC) analysis shows. Indeed, while a mixture prepared by simply mixing hyaluronic acid or a salt thereof with chondroitin sulphate or a salt thereof can be separated, this is not the case for the complex described in the present invention where the chondroitin sulphate or a salt thereof and hyaluronic acid or a salt thereof are intrinsically bounded.

The complex according to the invention can be characterized and differentiated from physical mixtures using standard analytical tools analyzing differences in physico-chemical properties or by methods known in the art per se, such as Fourier Transform Infrared spectra (FT-IR) and Atomic Force Microscopy. Said complex possesses entirely different physico-chemical properties compared to individual hyaluronic acid or a salt thereof, or chondroitin sulphate or mixtures thereof.

Surprisingly, the inventors have found that the disclosed complex obtained by the process described above, presents improved physicochemical properties such as reduced viscosity and increased stability and solubility when dissolved or dispersed in water, which differ from a solution containing mixtures prepared by simply mixing both compounds. This result is completely unexpected in that, as previously stated, simple addition of chondroitin sulphate to sodium hyaluronate in aqueous solution is known to dramatically increase the viscosity of the mixture. However, the inventors have proven that the complex of the present invention exhibits enhanced solution viscosity over the viscosity of a simple mixture comprising hyaluronic acid and chondroitin sulphate of the same concentration.

Accordingly, in its broadest aspect, the present invention relates to a complex obtainable by:
a) mixing hyaluronic acid or a salt thereof with chondroitin sulphate or a salt thereof,
b) forming an aqueous solution of said mixture, and
c) atomizing the resulting aqueous solution, wherein the hyaluronic acid or a salt thereof has an average molecular weight greater than 1,000,000 Daltons, and the chondroitin sulphate or a salt thereof has an average molecular weight from 5,000 to 50,000 Daltons.

In a preferred embodiment, the invention provides a complex obtainable by the process described and defined herein above, wherein the hyaluronic acid or a salt thereof has an average molecular weight greater than 1,200,000 Daltons.

In another preferred embodiment, the invention provides a complex obtainable by the process described and defined herein above, wherein the weight ratio of hyaluronic acid or a salt thereof, to chondroitin sulphate or a salt thereof is within the range comprised from 1:1 to 10:1 or from 1:1 to 1:10, Preferably, the weight ratio of hyaluronic acid or a salt thereof, to chondroitin sulphate or a salt thereof is 1:1, More preferably, the weight ratio of hyaluronic acid or a salt thereof, to chondroitin sulphate or a salt thereof is 1:10.

The present invention further provides stable solutions, dispersions or suspensions comprising the complex obtainable by the process described and defined herein above.

In another aspect, the present invention provides a pharmaceutical composition comprising the complex obtainable by the process described and defined herein above to be administered by a route selected from the group consisting of parenteral administration, oral administration and topical administration.

In a preferred embodiment, the pharmaceutical composition comprising the complex of the present invention can be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulphate, benzyl alcohol, ascorbic acid, and the like. The parenteral formulations can be stored in any conventional containers such as vials, ampoules and pre-filled syringes.

In another preferred embodiment of the invention, the pharmaceutical composition comprising the claimed complex can be administered parenterally, wherein the concentration of the complex is equal or greater than 20 mg/mL. Preferably, the pharmaceutical composition comprising the complex is formulated in the form of an aqueous solution or dispersion for intra-articular administration at a concentration greater than 20 mg/mL.

Thus, in one embodiment, the pharmaceutical composition comprising the complex of the present invention can be specially adapted for intra-articular use in the form of sterile solutions or suspensions. In addition to the afore-mentioned active agents, it can be appreciated by one of skill in the art that the pharmaceutical compositions comprising the complex of the invention adapted for intra-articular use can also comprise preservatives, pharmaceutically active carriers, excipients, stabilizers, buffers, antimicrobial growth inhibitors and the like and the use of such is contemplated by the invention. In particular, the pharmaceutical composition is adapted or formulated for intra-articular injection, intra-articular application or systemic use. Preferably, said pharmaceutical composition is suitable for intra-articular injection. In another preferred embodiment, the pharmaceutical composition for intra-articular injection comprises a high molecular weight hyaluronic acid or a salt thereof.

According to another aspect, the present invention relates to a sanitary, medical or surgical article comprising the pharmaceutical composition as described herein above. Preferably, said article is a pre-filled syringe for intra-articular application comprising the pharmaceutical composition as defined above. In another preferred embodiment, the pharmaceutical composition used in the pre-filled syringe for intra-articular application comprises a high molecular weight hyaluronic acid or a salt thereof.

In another aspect, the invention refers to an artificial matrix for intra-articular implantation comprising the pharmaceutical composition as described herein above. In a preferred embodiment, the pharmaceutical composition used in the artificial matrix for intra-articular implantation comprises a high molecular weight hyaluronic acid or a salt thereof.

In another preferred embodiment, the pharmaceutical composition comprising the complex obtainable by the process described and defined herein above is formulated or adapted for intra-articular irrigation. Preferably, said pharmaceutical composition is formulated in the form of an aqueous solution useful as intra-articular lavage liquid. In another preferred embodiment, the pharmaceutical composition comprising the claimed complex for intra-articular irrigation comprises a high molecular weight hyaluronic acid or a salt thereof.

Accordingly, in another preferred embodiment, the invention provides a pharmaceutical composition comprising the complex obtainable by the process described and defined herein above, for restoring synovial fluid elasticity and biological lubrication. Preferably, the pharmaceutical composition for restoring synovial fluid elasticity and biological lubrication comprises a high molecular weight hyaluronic acid or a salt thereof.

In a preferred embodiment, the pharmaceutical composition comprising the complex of the present invention can be administered orally. For oral delivery, said dried compound can be incorporated into a formulation that might includes acceptable carriers such as binders (e.g., gelatin, cellulose, gum tragacanth), excipients (e.g., starch, lactose), lubricants (e.g., magnesium stearate, dioxide), disintegrating agents (e.g., alginate, Primogel and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules. Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

In another preferred embodiment, the pharmaceutical composition comprising the complex of the present invention can be administered topically. Routes of topical administration include nasal, buccal, mucosal, rectal, or vaginal applications. For topical administration, said pharmaceutical composition can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown et al., *Ann. Rev. Med.* 39, 221-229 (1988) which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al., *J. Clin. Psych.* 45, 242-247 (1984). Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly (glycolic-co-L-lactic acid) may be useful. See, e.g., Phillips et al., *J. Pharmaceut. Set.* 73, 1718-1720 (1984).

Accordingly, the pharmaceutical composition comprising the complex of the present invention may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual) and parenteral (e.g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly).

In a preferred embodiment of the invention, the amount of complex in a pharmaceutical composition for oral administration is equal or greater than 220 mg.

In another preferred embodiment of the invention, the concentration of the complex in a pharmaceutical composition for topical administration is equal or greater than 70 mg/mL. Preferably, the pharmaceutical composition for topical administration comprises a complex at a concentration greater than 100 mg/mL.

Additionally, the invention provides a pharmaceutical composition comprising the complex of the invention and a pharmaceutically acceptable carrier, for use in the treatment and/or repair of joints, tendons and connective tissue disease or injuries. Examples of such joint, tendons or connective tissue disease or injury include without limitation, joint damage, injured tendons, arthritis, osteochondral lesions, osteoarthritis, tendonitis, tenosynovitis, bursitis and ligament injuries.

The invention further provides a pharmaceutical composition comprising the complex of the invention and a pharmaceutically acceptable carrier, for reducing pain and discomfort associated with joints, tendons and connective tissue disease or injuries.

Additionally, the invention provides a pharmaceutical composition comprising the complex of the invention and a pharmaceutically acceptable carrier, for use in the treatment of skin disease or injuries. Examples of such skin disease or injuries include without limitation, wound healing, ulcers, burns and dry skin.

In another preferred embodiment, the pharmaceutical composition comprising the complex of the present invention is formulated or adapted for ophthalmic use. Preferably, said pharmaceutical composition is adapted or formulated for topical ocular administration in the field of ophthalmology (e.g., eye drops, ocular inserts, ocular lubricants, tear gel, lid wipes, cleansing sterile wipes for the eyes, ophthalmic eye cleansing wipes and eye ointment).

As previously discussed, mixtures of hyaluronic acid or a salt thereof, and chondroitin sulphate are known to have utility in ophthalmologic and joint therapy. Those skilled in the art will appreciate, however, that such mixtures will have other utility beyond these uses. Accordingly, the pharmaceutical composition comprising the complex of the invention can be formulated or adapted for other uses including but not limited to drug delivery, (e.g. delivery of anti-fibrotics, antibiotics, steroidal and non-steroidal antiinflammatories, anesthetics, analgesics and other medicaments or gene therapies to diseased or traumatized tissues in need thereof) and cosmetics (e.g. the pharmaceutical composition may be formulated or adapted for injection to reduce wrinkles or to treat varicose veins).

According to another aspect, the invention further provides a composition comprising the complex as defined herein above for cosmetic use.

Similarly, the pharmaceutical composition comprising the complex of the present invention may be used in conjunction with other known therapies, compounds or formulations. For example, said pharmaceutical composition may be administered in combination with one or more other agents selected from antiinflammatories, antirheumatics, steroids and chondrogenic stimulating factors, either separately or in a single formulation.

The present invention also relates to a process for the preparation of complexes.

Accordingly, in another aspect, the invention relates to a process for obtaining a complex, comprising the steps of:
 a) mixing hyaluronic acid or a salt thereof with chondroitin sulphate or a salt thereof,
 b) forming an aqueous solution of said mixture, and
 c) atomizing the resulting aqueous solution.
wherein the hyaluronic acid or salt a thereof has a molecular weight greater than 1,000,000 Daltons, and the chondroitin sulphate or a salt thereof has an average molecular weight from 5,000 to 50,000 Daltons.

The embodiments described above are considered to be illustrative in all respects and not restrictive, the scope of the invention being indicated by the appended claims rather than by the foregoing description.

BRIEF DESCRIPTION OF THE FIGURES

For the purpose of better illustrating the advantages and properties of the complexes object of the invention, several graphs and images are attached as non-limiting examples.

DETAILED DESCRIPTION OF THE INVENTION

The terms "hyaluronan", "hyaluronate" or "hyaluronic acid" as used herein, refer to an acidic polysaccharide with different molecular weights constituted by residues of D-glucuronic and N-acetyl-D-glucosamine acids, which occur naturally in cell surfaces, in the basic extracellular substances of the connective tissue of vertebrates, in the synovial fluid of the joints, in the endobulbar fluid of the eye, in human umbilical cord tissue and in rooster' combs. It can be appreciated by one of skill in the art that the hyaluronic acid can be selected from among any of a number of commercially available sources.

The terms "high molecular weight hyaluronic acid", ""high molecular weight hyaluronan" or ""high molecular weight hyaluronate", refer to "hyaluronan", "hyaluronate" or "hyaluronic acid" as defined herein above, having a molecular weight of not less than about 1,000,000 Daltons (Mw≥$10^6$ Da or 1 MDa).

All numbers herein expressing "molecular weight" of hyaluronic acid or a salt thereof, and chondroitin sulphate or a salt thereof are to be understood as indicating the average molecular weight (Mw) in Daltons.

Salts of hyaluronic acid include without limitation sodium hyaluronate, potassium hyaluronate, magnesium hyaluronate, calcium hyaluronate and combination thereof.

The term "chondroitin sulphate" refers to a glycosaminoglycan constituted by alternate disaccharide sequences of differently sulfated residues of D-glucuronic acid and of N-acetyl-D-galactosamine. Depending on the disaccharide nature, chondroitin sulfates with different carbohydrate backbones are known, namely chondroitin 4-sulphate, chondroitin 6-sulphate and mixtures thereof, optionally in presence of other existing forms of chondroitin sulphate known in the state of the art. The preferred chondroitin sulphate is rich in chondroitin 4-sulphate disaccharides.

Salts of chondroitin sulphate include without limitation sodium chondroitin sulphate, potassium chondroitin sulphate, magnesium chondroitin sulphate, calcium chondroitin sulphate, lithium chondroitin sulphate and combinations thereof.

The term "complex" as used herein, refers to a structure consisting of a molecule weakly connected to surrounding atom(s) or molecule(s), wherein the molecule(s) or atom(s) are interconnected to each other non-covalently by any connective forces. The term encompasses any molecular entity formed by loose association involving hyaluronic acid or a salt thereof, and chondroitin sulphate or a salt thereof; thereby said structure exhibits at least one physico-chemical property different from individual components or mixtures thereof.

The term "forming a solution" or "solution" means obtaining a solution of a substance (e g, the complex of the present invention) in a solvent in any manner. It encompasses partial solutions.

As explained above, the complex of the present invention is structurally different from a simple mixture of sodium hyaluronate (HA) and chondroitin sulphate (CS) and therefore it is not a simple mixture of both compounds. The complex of the present invention can be identified and differentiated from a simple mixture of sodium hyaluronate and chondroitin sulphate by FT-IR spectroscopy. FT-IR spectroscopy was carried out using an ABB FTLA 2000 instrument coupled to a Spectratech microscope. Samples were analyzed with KBr aplitter, Glowbar source and MCT detector. The spectral range was 4000-720 $cm^{-1}$ with a 4 $cm^{-1}$ resolution, HA and CS controls, a HA:CS mixture and the atomized complex were grinded and compressed on a diamond cell for analysis.

Figure 1:
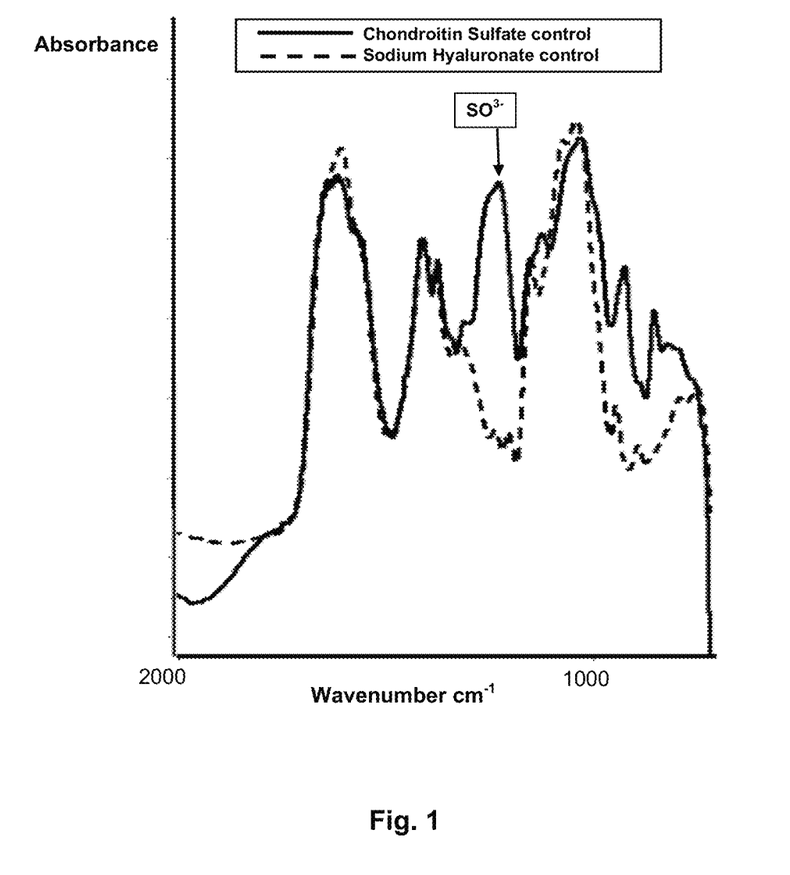
FIG. 1 shows the Fourier Transform InfraRed spectrum (FT-IR) of sodium hyaluronate and chondroitin sulphate.
Figure 2:
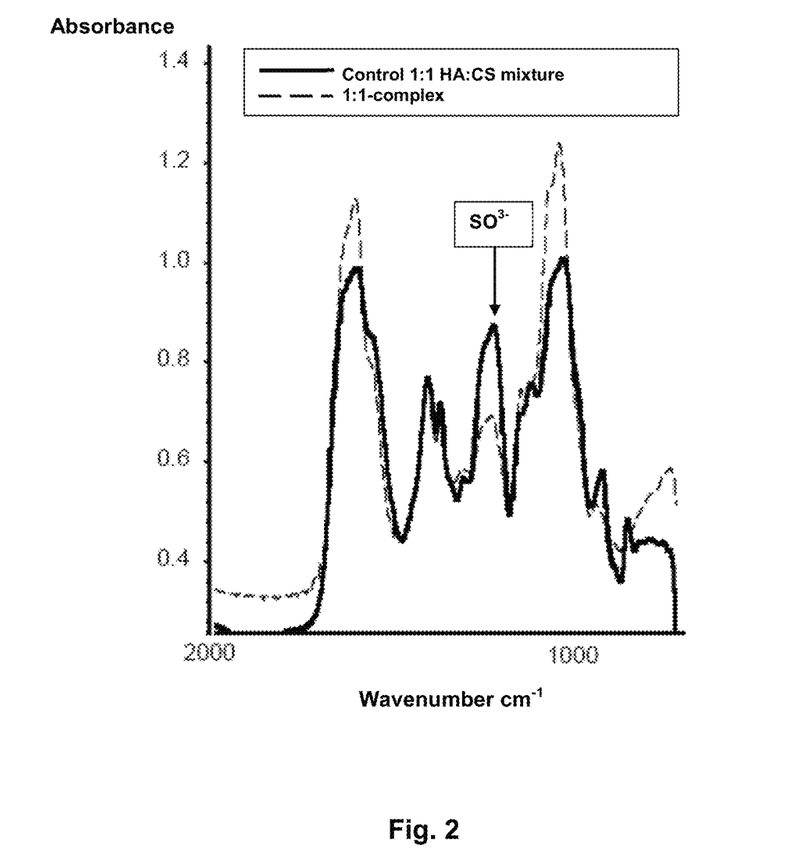
FIG. 2 shows the FT-IR spectrum of a 1:1 mixture of sodium hyaluronate and chondroitin sulphate and of the complex according to the invention.

The FT-IR spectrum of chondroitin sulphate (FIG. 1) displays a distinctive band at 1240 $cm^{-1}$, corresponding to the C—O—$SO^{3-}$ group. This intense band at 1240 $cm^{-1}$ can be also seen in the FT-IR spectrum of a 1:1 mixture of sodium hyaluronate and chondroitin sulphate (FIG. 2). However, the spectrum of the 1:1 complex obtained by atomization as described in example 1 below does not display such an intense band characteristic of the C—O—$SO^{3-}$ group present in chondroitin, said band is significantly reduced in the complex obtained by atomization, indicating a change in conformation of the components.

Furthermore, z-potential analyses were performed to characterize the surface charge of the complex of the present invention. Results show that the z-potential of a 1:1 HA:CS simple mixture is significantly different to the one obtained with the complex, confirming that they are structurally different entities with different surface charge (Table 1).

Samples were weighed and suspended in isopropyl alcohol to a final concentration of 20 mg/mL. Experiments were run on a Nano-Z zetasizer (Malvern Instruments), at 25° C. using a clear disposable zeta cell. Z-potential of suspended samples was analyzed to simulate a solid state measurement.

TABLE 1

|  | Z Potencial mV |
|---|---|
| (1:1) HA:CS mixture | −1 |
| Complex | −13.8 |

Another property related to the surface charge and ion mobility of polyelectrolytes is conductivity. Conductivity in solution was obtained dissolving the samples in water at a final concentration of 10 mg/mL. The conductivity of the complex in solution is significantly lower than the conductivity of a simple mixture, indicating a change in conformation due to differences in electric conductivity and ion mobility (Table 2).

TABLE 2

|  | Conductivity mS/m |
|---|---|
| (1:1) HA:CS mixture | 1.45 |
| Complex | 1.01 |

Figure 4:
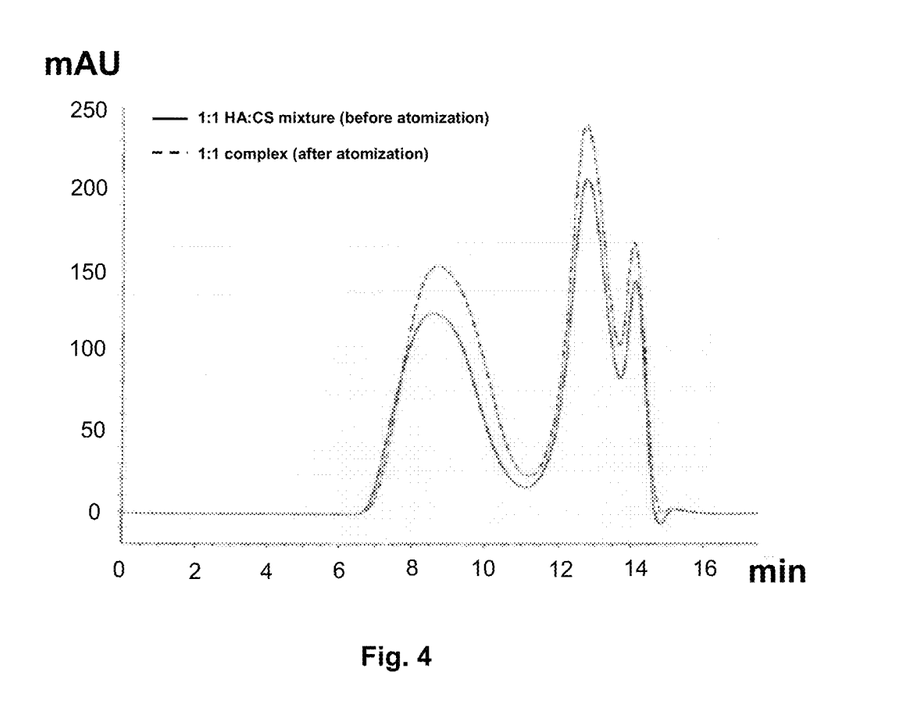
FIG. 4 shows high performance liquid chromatography (HPLC) of a 1:1 mixture of sodium hyaluronate and chondroitin sulphate and the complex.

Moreover, quantitative determination of a 1:1 mixture of sodium hyaluronate and chondroitin sulphate and a 1:1 complex obtained by atomization was performed by HPLC. Samples were reconstituted in Milli-Q water at a final concentration of 1 mg/mL. 30 µl of samples was injected into an Agilent 1200 HPLC, equipped with a DAD detector using an Ultrahydrogel 2000 size exclusion chromatography column (12 µm pore size, 77.8×300 mm, Waters) maintained at 45° C. Samples were eluted using a phosphate buffer 50 mM, pH 5.5 mobile phase at a flow rate of 0.8 mL/min. The detector was set at 200 nm. FIG. 4 shows the chromatograms before and after atomization. Both samples show two peaks corresponding to HA and CS with retention times of 8.57 and 12.8 min respectively. After atomization no significant changes in molecular weight and retention times are observed, indicating that both compounds maintain their individual chemical characters in comparison with HA and CS alone.

Figure 3:
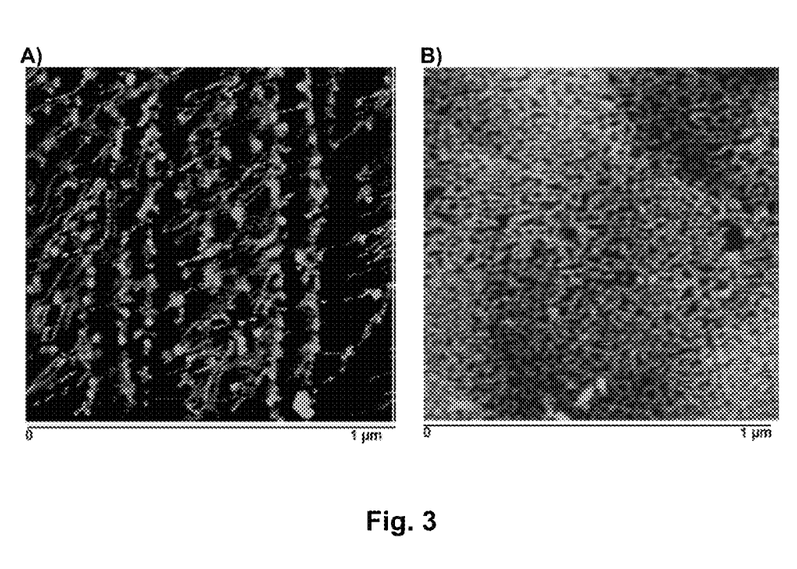
FIG. 3 shows atomic force microscopy images of a 1:1 sodium hyaluronate and chondroitin sulphate mixture and of a complex.

In addition, the complex was analyzed under Atomic Force Microscopy. AFM images were acquired on an AFM Dimension 3100 microscope with a Nanoscope IV an electronic controller in Tapping Mode, using a Vistaprobe AFM tip with a 40 nN/nm spring constant. The 1:1 HA:CS complex obtained according to the invention and a 1:1 sodium hyaluronate/chondroitin sulphate mixture were dissolved in water at 20 mg/mL, incubated overnight (4° C.) and then diluted to a final concentration of 20 µg/mL. Then, 20 µl were deposited onto freshly cleaved Highly Ordered Pyrolytic Graphite (HOPG) for 60-180 seconds, rinsed with Milli-Q water and gently dried under a nitrogen stream. FIG. 3(B) shows that the complex has a highly dense intricate network of interacting polymer chains in comparison with a simple mixture of sodium hyaluronate and chondroitin sulphate (FIG. 3(A)) which displays a non-ordered structure with non-interacting polymeric chains. This indicates that the complex of the present invention has a different molecular conformation than a simple mixture of chondroitin sulphate or a salt thereof and hyaluronic acid or a salt thereof The above results demonstrate that the atomization process affects the conformation of the molecules, obtaining a complex with different physico-chemical properties than a simple mixture of sodium hyaluronate and chondroitin sulphate.

Moreover, the inventors have found that said complex obtained by the process described and defined herein above have unexpected improved physicochemical properties with respect to a simple mixture. For example, viscosity measurements by rheological techniques show that the atomization process causes a decrease in viscosity of the complex obtained, which indicates a change of conformation in the complex ultrastructure.

Aqueous solutions of HA:CS mixtures (control) and atomized complexes at different weight ratios of sodium hyaluronate and chondroitin sulphate were prepared for rheological characterization. Their rheological profile was determined using a HAAKE RheoStress RS300 rheometer in stress controlled mode. A 1° cone and 35 mm diameter plate was used.

Controls and 1:1 and 1:10 complexes were reconstituted in Milli-Q water. Samples concentrations are summarized in Table 3.

TABLE 3

| Sample | Composition | Concentration |
|---|---|---|
| 1 | Control HA | 10 mg/mL |
| 2 | Atomized HA | 10 mg/mL |
| 3 | Control (1:1) HA:CS mixture | 20 mg/mL |
| 4 | (1:1) Complex | 20 mg/mL |
| 5 | Control (1:10) HA:CS mixture | 110 mg/mL |
| 6 | (1:10) Complex | 110 mg/mL |

Based on an applied shear stress, viscosity of the samples was measured at 25° C. All samples fitted in a Cross model, which allowed to compare the results obtained.

The viscosity profiles for each composition are shown in Table 4.

TABLE 4

Apparent viscosities obtained for samples at different shear rates

| | Viscosity (mPa · s)/Viscosity loss* (%) | | | |
|---|---|---|---|---|
| Sample | $\gamma = 1$ | $\gamma = 10$ | $\gamma = 100$ | $\gamma = 200$ |
| 1 | 4884.3 | 2307.0 | 578.0 | 375.0 |
| 2 | 3378.5/(30.8) | 1924.5/(16.5) | 522.0/(9.6) | 326.5/(12.9) |
| 3 | 3934.7 | 2004.3 | 550.0 | 359.0 |
| 4 | 3061.0/(22.2) | 1751.0/(12.6) | 527.0/(4.1) | 341.0/(5.0) |
| 5 | 5569.5 | 2438.0 | 633.5 | 400.5 |
| 6 | 4824.0/(13.3) | 2390.5/(1.9) | 736.0 | 488.5 |

$\gamma$ = Shear rate s$^{-1}$
*Difference in viscosity of a sample with respect its control Rheometry data shows that at shear rate of 1 s$^{-1}$ the apparent viscosity of the atomized products (HA, Complex (1:1) and Complex (1:10)) give a significant decrease in viscosity (30.8%, 22.2% and 13.3% respectively) compared to their corresponding non-atomized controls (simple mixtures).

Indeed, a 1:1 atomized complex in solution has a 22.2% drop in viscosity with respect to an aqueous solution of a HA:CS simple mixture of the same concentration and weight ratio. This reduction in viscosity, allows formulations based on a 1:1 complex with up to a 25% concentration increase of both compounds in solution with respect to conventional formulations comprising simple mixtures of sodium hyaluronate and chondroitin sulphate.

This is of considerable interest because it allows increasing the concentration or molecular weight of both compounds in a formulation while maintaining the optimal rheological properties for some applications such as intra-articular-injection.

Moreover, the claimed complex obtainable by the process described in the present invention, exhibits a viscosity in aqueous solution (e.g. solubilization of the product obtained in step c) lower than the viscosity of an aqueous solution containing a simple mixture of hyaluronic acid or a salt thereof, and chondroitin sulphate or a salt thereof of the same concentration (e.g. the aqueous solution of step b). The drop in viscosity obtained with the complex in solution is greater than 5%, even greater than 10%, with respect to an aqueous solution of a mixture of hyaluronic acid or a salt thereof, and chondroitin sulphate or a salt thereof of the same concentration (see Table 4).

In the process of the present invention, the compositions to be atomized or feed (or feed stock) can be any solution, coarse suspension, slurry, aqueous mixture, colloidal dispersion, or paste comprising hyaluronic acid or a salt thereof, and chondroitin sulphate or a salt thereof, that may be atomized using a selected spray drying apparatus. Typically, the feed is sprayed into a current of hot air that evaporates the solvent and conveys the dried product to a collector. The atomizer can be, for example, a rotary atomizer or a two-fluid mixing nozzle. Those skilled in the art will appreciate that, several different types of apparatus may be used to provide the desired product. Provided that complexes comprising the correct morphology and/or composition are produced, the choice of apparatus is not critical and would be apparent to the skilled artisan in view of the teachings herein.

The last step of the claimed process, namely, the atomization step, is usually performed at a temperature comprise between 80° C. and 150° C. (inlet temperature), preferably between 100° C. and 150° C. In the following example, the atomization step was performed at an inlet temperature of 120° C.

The following examples are provided to further illustrate the complex according to the present invention and various compositions comprising said complex obtained in accordance with example 1 below. The examples provided below are illustrative and are not intended to limit the scope of the claimed invention.

Example 1

Preparation of a Complex

Solutions of sodium hyaluronate (HA) of biotechnological origin (Mw>1200 KDa, obtained from CPN) and chondroitin sulphate (CS) of bovine origin (Mw 5-50 KDa, mean Mw 20 KDa from Derquimica) were prepared by mixing both components at ratios 1:1 and 1:10 (w/w, HA:CS). The resultant mixture was then dissolved in Milli-Q autoclaved water and stirred at 500 rpm for 4 h at room temperature. Samples were kept for 12 hours at 4° C., before evaporation of the water by atomization.

Samples were first diluted to obtain a viscosity ≤2000 mPa·s and then subjected to atomization in a Buchi Mini Spray drier B-290 under the following conditions: volume 140-170 mL, aspiration 90%, inlet temperature 120° C., and outlet temperature 73° C. HA:CS dried samples were kept at 4° C. for further analysis.

Example 2

Viscoelastic Composition for Intra-Articular Injection

| | |
|---|---|
| 1:1 HA:CS complex | 60 mg/ml |
| Mannitol | 5 mg/ml |

A number of products comprising sodium hyaluronate and chondroitin sulphate are available on the market. For example, Arthromac® is an injectable gel indicated for the treatment of osteoarthritis (OA) containing 21 mg/mL of sodium hyaluronate and 28 mg/mL of chondroitin sulphate. Other commercial products without chondroitin sulphate contain hyaluronate in concentrations between 8 and 25 mg/mL (for example, Jointex®, Ostenil®, Suplasyn®, Hyalgan®, Coxarthrum®).

The inventors of the present invention were able to formulate a viscoelastic composition for intra-articular injection comprising the complex of the present invention with a concentration of 60 mg/mL, which represents a substantially higher concentration of sodium hyaluronate and chondroitin sulphate in comparison with known formulations available on the market.

Therefore a composition comprising the complex of the present invention can produce an improved long-term therapeutic effect implying fewer injections. This allows treating in a very efficient manner articular diseases or injuries without the disadvantage of injecting several doses per day.

Example 3

Oral Formulation

| | |
|---|---|
| Purified water | 64.4 g |
| Fructose | 29.5 g |
| Maltodextrin | 1 g |
| Pregelatinized starch | 1.8 g |
| Citric acid (anhydrous) | 1.2 g |
| Potassium sorbate | 0.28 g |
| 1:1 HA:CS Complex | 0.6 g |
| Raspberry flavor | 0.057 g |
| Colloidal dilicium dioxide | 0.1 g |
| Sodium chloride | 1 g |
| Antifoaming | 0.043 g |
| Cellulose | 0.006 g |

Example 4

Topical Gel

| | |
|---|---|
| Water | 48.15% |
| *Aloe Vera* gel | 12% |
| Glycerin | 10% |
| Paraffinum liquidum | 5% |
| Sodium hydroxide | 3.5% |
| 1:1 HA:CS complex | 20% |
| Carbomer | 0.85% |
| Phenoxyethanol, Methylparaben, Butylparaben, Propylparaben, Isobutylparaben | 0.5% |

The invention claimed is:

1. A dried product obtained by a method consisting essentially of:
   a) mixing a solid hyaluronic acid or a salt thereof with a solid chondroitin sulphate or a salt thereof at room temperature to form a solid mixture,
   b) forming an aqueous solution of said solid mixture at room temperature, and
   c) atomizing the resulting aqueous solution to form a dried product,
   wherein the hyaluronic acid or a salt thereof has an average molecular weight greater than 1,000,000 Daltons, and the chondroitin sulphate or a salt thereof has an average molecular weight from 5,000 to 50,000 Daltons,
   wherein an aqueous solution of the dried product has a viscosity lower than an aqueous solution of the hyaluronic acid or a salt thereof and the chondroitin sulphate or a salt thereof, and
   wherein an aqueous solution of the dried product at a concentration of 10 mg/mL has a conductivity lower than an aqueous solution of a mixture of the hyaluronic acid or a salt thereof and the chondroitin sulphate or a salt thereof at a concentration of 10 mg/mL.

2. The dried product according to claim 1, wherein the hyaluronic acid or a salt thereof has an average molecular weight greater than 1,200,000 Daltons.

3. The dried product according to claim 1, wherein the weight ratio of hyaluronic acid or a salt thereof to chondroitin sulphate or a salt thereof is from 1:1 to 1:10.

4. The dried product according to claim 3, wherein the weight ratio of hyaluronic acid or a salt thereof to chondroitin sulphate or a salt thereof is 1:1.

5. A pharmaceutical composition comprising the dried product as defined in claim 1 to be administered by a route selected from the group consisting of parenteral administration, oral administration and topical administration.

6. The pharmaceutical composition according to claim 5, wherein a concentration of the dried product to be administered parenterally is equal or greater than 20 mg/mL.

7. The pharmaceutical composition according to claim 5, wherein said composition is administered by intra-articular injection.

8. The pharmaceutical composition according to claim 5, wherein an amount of dried product to be administered orally is equal or greater than 220 mg.

9. The pharmaceutical composition according to claim 5, wherein a concentration of the dried product to be administered topically is equal or greater than 70 mg/mL.

10. A pre-filled syringe for intra-articular application comprising the pharmaceutical composition according to claim 5.

11. An artificial matrix for intra-articular implantation comprising the pharmaceutical composition according to claim 5.

12. A pharmaceutical composition according to claim 5, for use in restoring synovial fluid or for intra-articular irrigation.

13. A pharmaceutical composition comprising the dried product as defined in claim 1 for use in the treatment and/or repair of joints, tendons and connective tissue disease or injuries.

14. A cosmetic composition comprising the dried product as defined in claim 1.

15. A dried product consisting essentially of an atomized aqueous solution prepared from a mixture of a solid hyaluronic acid or a salt thereof and a solid chondroitin sulphate or a salt thereof dissolved in an aqueous solution, wherein the hyaluronic acid or a salt thereof has an average molecular weight greater than 1,000,000 Daltons, and the chondroitin sulphate or a salt thereof has an average molecular weight from 5,000 to 50,000 Daltons, wherein an aqueous solution of the dried product has a viscosity lower than an aqueous solution of the hyaluronic acid or a salt thereof and the chondroitin sulphate or a salt thereof and wherein an aqueous solution of the dried product at a concentration of 10 mg/mL has a conductivity lower than an aqueous solution of a mixture of the hyaluronic acid or a salt thereof and the chondroitin sulphate or a salt thereof at a concentration of 10 mg/mL.

16. A pharmaceutical composition comprising the dried product of claim 15 and a pharmaceutically acceptable carrier.

17. A cosmetic composition comprising the dried product of claim 15 and a cosmetically acceptable carrier.

18. A process for preparing a dried product consisting essentially of the steps of:

a) mixing a solid hyaluronic acid or a salt thereof with a solid chondroitin sulphate or a salt thereof at room temperature to form a solid mixture, b) forming an aqueous solution of said solid mixture at room temperature, and c) atomizing the resulting aqueous solution, wherein the hyaluronic acid or a salt thereof has a molecular weight greater than 1,000,000 Daltons, and the chondroitin sulphate or a salt thereof has an average molecular weight from 5,000 to 50,000 Daltons, wherein an aqueous solution of the dried product has a viscosity lower than an aqueous solution of the hyaluronic acid or a salt thereof and the chondroitin sulphate or a salt thereof, and wherein an aqueous solution of the dried product at a concentration of 10 mg/mL has a conductivity lower than an aqueous solution of a mixture of the hyaluronic acid or a salt thereof and the chondroitin sulphate or a salt thereof at a concentration of 10 mg/mL.

\* \* \* \* \*